(12) United States Patent
Maier et al.

(10) Patent No.: US 8,237,107 B2
(45) Date of Patent: Aug. 7, 2012

(54) SPECTROPHOTOMETRIC IDENTIFICATION OF MICROBE SUBSPECIES

(75) Inventors: Thomas Maier, Leipzig (DE); Markus Kostrzewa, Taucha (DE)

(73) Assignee: Bruker Daltonik GmbH, Bremen (DE)

( * ) Notice: Subject to any disclaimer, the term of this patent is extended or adjusted under 35 U.S.C. 154(b) by 118 days.

(21) Appl. No.: 12/834,504

(22) Filed: Jul. 12, 2010

(65) Prior Publication Data

US 2011/0012016 A1 Jan. 20, 2011

(30) Foreign Application Priority Data

Jul. 10, 2009 (DE) .................. 10 2009 032 649

(51) Int. Cl.
*B01D 59/44* (2006.01)
*H01J 49/00* (2006.01)

(52) U.S. Cl. .......... 250/282; 250/281; 250/397; 702/19; 702/27; 435/5

(58) Field of Classification Search .......... 250/281–283, 250/287, 288, 290–293, 397; 702/19, 23, 702/27; 435/5
See application file for complete search history.

(56) References Cited

U.S. PATENT DOCUMENTS

| | | | |
|---|---|---|---|
| 7,391,017 B2 | 6/2008 | Kostrzewa et al. | |
| 2004/0234952 A1* | 11/2004 | Kallow et al. | 435/5 |
| 2010/0255527 A1* | 10/2010 | Weller | 435/29 |
| 2011/0202282 A1* | 8/2011 | Kostrzewa | 702/19 |
| 2011/0272573 A1* | 11/2011 | Kostrzewa et al. | 250/282 |
| 2012/0009558 A1* | 1/2012 | Armstrong et al. | 435/3 |

FOREIGN PATENT DOCUMENTS

| | | |
|---|---|---|
| DE | 10038694 | 2/2002 |
| DE | 10300743 | 7/2004 |
| EP | 1253622 | 10/2002 |
| WO | 2008151140 | 12/2008 |

OTHER PUBLICATIONS

Jarman et al., "Extracting and visualizing matrix-assisted laser desorption/ionization time-of-flight mass spectral fingerprints", Rapid Communications in Mass Spectrometry 13 (1999), pp. 1586-1594.

Barbuddhe et al., "Rapid Identification and typing of listeria species by matrix-assisted laser desorption ionization-time of flight mass spectrometry", Applied and Environmental Microbiology 74 (2008), pp. 5402-5407.

van Baar, Ben. "Characterisation of Bacteria by Matrix-Assisted Laser Desorption/Ionisation and Electrospray Mass Spectrometry", FEMS Microbiology Reviews vol. 24 (2000), pp. 193-219.

Jarman et al. "An Algorithm for Automated Bacterial Identification Using Matrix-Assisted Laser Desorption/Ionization Mass Spectrometry", Analytical Chemistry, vol. 72, No. 6, Mar. 15, 2000, pp. 1217-1223.

* cited by examiner

*Primary Examiner* — Bernard E Souw
(74) *Attorney, Agent, or Firm* — O'Shea Getz P.C.

(57) ABSTRACT

A dual-stage method is provided for identifying a microbe by, for example, its species or its subspecies. The method includes measuring a mass spectrum of the microbe using a mass spectrometer, calculating indicators for similarities between reference mass spectra in a library and the measured mass spectrum, selecting a group of reference mass spectra similar to the measured mass spectrum, determining a distinguishing weight for each mass signal of the reference mass spectra in the group, where the distinguishing weights emphasize differences between the reference mass spectra in the group, and calculating indicators for similarities between the reference mass spectra in the group and the measured mass spectrum as a function of the distinguishing weights.

17 Claims, 1 Drawing Sheet

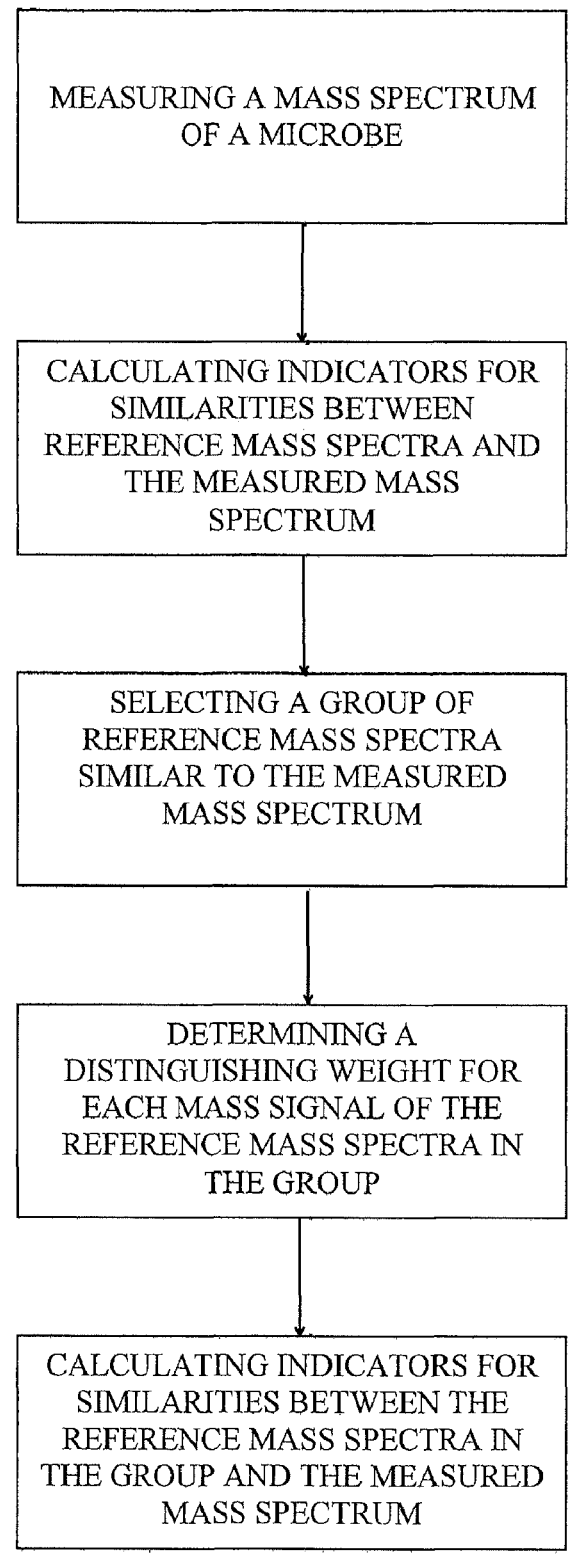

SPECTROPHOTOMETRIC IDENTIFICATION OF MICROBE SUBSPECIES

PRIORITY INFORMATION

This patent application claims priority from German Patent Application 10 2009 032 649.9 filed on Jul. 10, 2009, which is hereby incorporated by reference.

FIELD OF THE INVENTION

The invention relates to identifying microbes by mass spectra using similarity comparisons with reference mass spectra in spectrum libraries.

BACKGROUND OF THE INVENTION

Methods for fast, error-free identification of microorganisms (or microbes) play an important role during, for example: clinical and extra-clinical infection diagnostics; hygiene monitoring in hospitals and at rivers and lakes used for swimming; food analysis; monitoring and controlling biotechnical processes; and microbiological research. Many institutes worldwide collect various strains of vacuum-dried or deep-frozen microbes for such identifications.

The term "microorganism" or "microbes" describes microscopically small organisms and some viruses. The organisms can include, for example, bacteria, unicellular fungi (e.g., yeasts), algae, and protozoae (e.g., plasmodia as malaria pathogens). Microbes are typically categorized according to the following taxonomic hierarchical scheme: domain (eukaryotes and prokaryotes), kingdom, phylum, class, order, family, genus, species and subspecies. Occasionally additional taxonomic class(es), e.g., serovars or serotypes, are used for differentiating microbes, such as bacteria, included within a subspecies. Serovars and serotypes are distinguished by their different types of attachment behavior at a cell membrane.

The genus and typically the species are determined in order to identify a microbe sample. When possible, the subspecies, the serotype and/or the strain are also determined for the microbe identification. Alternatively, a microbe sample may be identified using other distinguishing characteristics such as pathogenicity of the microorganism (i.e., the ability to bring on an illness), or resistance of the microorganism against antibiotics.

Traditionally, colonies of a sampled microorganism are cultivated in order to determine the identity thereof. "API Tests" used in laboratories, for example, include different culture media for microbe cultivation. Each culture media can detect a specific metabolic characteristic of a microorganism, which permits an initial, approximate taxonomic classification of the microorganism. Microscopic morphology of individual organisms in the colony and the morphology of the colony itself can also be determined. Other types of identification methods can also be used such as: (i) a DNA or a RNA sequence analysis after replication of specific genetic sequences by polymerase chain reaction (PCR), or (ii) a mass spectrometric detection of specific molecular cell components of microorganisms. These alternative methods are generally considered superior to the aforesaid cultivation method for their specificity (true-negative rate), sensitivity (true-positive rate), other error rates and analytical speed.

A publication by van Baar (FEMS Microbiology Reviews, 24, 2000, 193-219: "Characterization of bacteria by matrix-assisted laser desorption/ionization and electrospray mass spectrometry"), describes one example of a mass spectrometric measurement method for bacteria identification. The identification is determined by analyzing similarities between a mass spectrum of the bacteria and reference spectra for known bacteria. During the analysis, a similarity indicator is assigned to each of the reference spectra. The similarity indicator is a measure of agreement between the reference spectrum and the mass spectrum of the sample. The bacterium is identified when, for example, the similarity indicator is significantly larger than similarity indicators for all other reference spectra, and is also larger than a specified minimum value.

The reference spectra are usually collected in a library, which may include reference spectra of bacteria and other microbes, such that bacteria and other types of microorganisms may be identified. Official directives prescribe a distinct validation of medical and forensic reference spectra libraries. Validations typically require each entry be traceable and accurately documented. The reference spectra are obtained from accurately characterized and identified strains. The strains of microorganisms are collected worldwide in government, public and private institutes, usually stored in a deep-frozen or vacuum-dried state, and made available for scientific purposes. Some microbiology institutes also catalog newly discovered strains of microbes. Although the exact classification of certain microbes may be disputed, these disputes are not detrimental to the value of the strains.

The term "strain" describes a microbe population that has been multiplied from a single organism. The individual organisms of the strain are genetically identical. As set forth above, the strains are cataloged in spectral libraries and have known (albeit sometimes disputed or changed) identities and classifications. In other words, each cataloged strain is identified as belonging to a known species and, where available, a known subspecies. Since microbes are collected and stored at different locations worldwide, many libraries have the same subspecies of certain strains. Although these strains are classified as having the same subspecies, however, there may be slight differences in the mass spectra of the same strain in different libraries. This indicates that there can be individual differences (such is the case with animals or plants of the same species) or even further branches of the hierarchy scheme such as, for example, serotypes. The strains are designated by internationally agreed labels after the name of the species or subspecies.

During a mass spectra measurement process, a colony of microbes is disposed on a solid, gelatinous nutrient medium or a centrifuge sediment (pellet) from a liquid nutrient medium. A small swab is used to transfer a tiny quantity of microbes from the colony or the sediment to a mass spectrometric sample support. A strongly acidified solution of a conventional matrix substance is sprinkled onto the sample. The matrix substance is used during a subsequent ionization by matrix-assisted laser desorption (MALDI). The acid of the matrix solution attacks the cell walls, and the organic solvent penetrates the microbial cells. Osmotic pressure causes the cell walls to burst and to release soluble proteins. The burst sample is dried and the dissolved matrix material crystallizes. The soluble proteins and, to a much lesser extent, other substances are also embedded into the matrix crystals.

In some cases, the cell walls of the microbes are difficult to destroy or are not destroyed by the matrix solution. In these cases, additional strong acids may be added to the matrix solution. The solution may also be sonically or mechanically treated to destroy the microbial cell wall. This procedure generates mass spectra that are similar to the spectra generated using the usual preparation on sample supports. The libraries of reference spectra can include reference spectra for both preparation methods.

The sample preparations dried on sample supports, i.e., the matrix crystals with the embedded analyte molecules, are inserted into an ion source of a mass spectrometer and bombarded with pulsed UV laser light. The pulsed UV laser light creates ions of analyte molecules which can be separated by mass in the mass spectrometer and measured. This type of ionization by matrix-assisted laser desorption is usually referred to as Matrix-Assisted Laser Desorption and Ionization (MALDI). Several types of commercial MALDI time-of-flight mass spectrometers are commercially available.

Today, mass spectra of microbe proteins are typically obtained using time-of-flight mass spectrometers operated in a linear mode. The mass spectra are obtained without using an energy focusing reflector because the linear mode exhibits a particularly high detection sensitivity, even though mass resolution and mass accuracy of the spectra from time-of-flight mass spectrometers in a reflector mode is greater. Specifically, approximately one twentieth of the ion signals appear in the reflector mode and the detection sensitivity is one to two powers of ten less than that in the linear mode. The linear mode of a time-of-flight mass spectrometer has a high sensitivity because the stable ions and the fragments from so-called "metastable" decays of the ions are detected. Secondary electron multipliers (SEM) are used in these mass spectrometers such that the neutral particles from ion disintegrations may be measured with the ion detector, because the neutral particles also generate secondary electrons on impact. The fragment ions and the neutral particles, which originated from one species of a parent ion, have the same speed as the parent ions and thus arrive at the ion detector at the same time. The time of flight of the fragment ions and the neutral particles is a measure of the mass of the originally undecayed ions.

The disadvantages associated with linear operation of time-of-flight mass spectrometers, for example significantly lower mass resolution and reduced mass accuracy, are typically outweighed by the need for high detection sensitivities. In order to increase the ion yield during linear operation, desorbing and ionizing laser energy is increased. The increase in the desorbing and ionizing laser energy, however, can also increase ion instability. The masses of individual mass signals can be shifted slightly from spectrum to spectrum due to poor reproducibility of the desorption and the ionization processes during the generation of the ions in a MALDI time-of-flight mass spectrometer operated in a linear mode. The mass shifts in the mass scales of the repeat spectra can be readjusted before the repeat spectra are combined to a reference spectrum. Such a readjustment method is disclosed in U.S. Pat. No. 7,391,017 to M. Kostrzewa et al., which is hereby incorporated by reference. The mass scales of sample and reference spectra can also be adjusted with respect to one another. Smaller mass tolerance intervals therefore can be used to determine matching mass signals during the similarity analysis.

The mass spectrum of microbes is equivalent to frequency profiles of mass values of the ions. The mass spectra for protein ions are usually obtained in the mass range between 2,000 daltons to 20,000 daltons. The mass spectra used for identifications are predominantly obtained in the mass range between around 3,000 daltons to 15,000 daltons. The reduced resolution indicates that the mass signals can no longer be resolved individually in the aforesaid mass range, rather each isotope group forms a single fused mass signal. Typically, the protein ions have a single charge (charge number $z=1$). Ions can therefore be referred to using their mass m, rather than using the more accurate "mass-to-charge ratio" m/z.

Each laser light pulse produces a single mass spectrum. The mass spectrum, however, merely includes signals for a few hundred to a few thousand ions. Typically, a few tens to a few hundreds of these individual mass spectra are added up to form a sum mass spectrum in order to provide greater reliability and less noise. The individual mass spectra can originate from different parts of the sample preparation or even from different sample preparations. The term "mass spectrum of a microbe" or "microbe spectrum" is used hereinafter to represent the aforesaid summation of the mass spectrums.

Each genetically predetermined protein has a characteristic mass. The profile of each of the proteins represented by the microbe spectrum therefore is characteristic of the microbe species. An abundance of individual proteins, which can be measured via mass spectrometry, in the microbes are typically genetically determined because their production is controlled by other proteins. Furthermore, they only slightly depend on the nutrient medium or the degree of maturity of the colony, which is quite different from the abundance of fatty acids that do not occur in the mass spectrum. The protein profiles therefore can identify microbes much like fingerprints can identify humans.

Mass spectra collected for colonies or sediments of microbes from accurately documented strains are produced and mass spectra acquired in order to provide reference spectra for a spectral library. Repeat spectra (i.e., multiple copies of a particular mass spectra) are typically collected for each reference spectrum. The mass spectra for each microbe typically includes between around 50 to 200 separated mass signals. Many of the mass signals however are pure noise because during the search for mass signals the ion detector is set to high sensitivity. The reference spectra are therefore usually reduced to a maximum number of 70 or 100. The information content is relatively high for a mass spectrum with 50 mass signals in the mass range between 3,000 to 15,000 daltons even without accounting for intensity differences because more than 2,000 distinguishable mass signals can occur even at a reduced mass resolving power. The repeat spectra are initially combined to an average spectrum rich in signals. When a limit between, for example, 70 to 100 mass signals has been reached, the mass signals which occur once or a few times in the repeat spectra are deleted. The mass signals with very low intensities are then deleted until the desirable maximum number of mass signals remains.

The mass spectra of the microbe samples (hereinafter "sample spectra") are typically generated in a similar way from repeat spectra and limited to a predetermined number of mass signals in order to exclude noise signals as best as possible. The number of mass signals in the sample spectra is usually selected to be slightly higher than the number of reference spectra.

The publication by Jarman et al. (Analytical Chemistry, 72(6), 2002, 1217 1223, entitled "An Algorithm for Automated Bacterial Identification Using Matrix-Assisted Laser Desorption/Ionization Mass Spectrometry" discloses a computational method for the generation of reference spectra of a library and for the similarity analysis between a sample spectrum and the reference spectra of a library. The method is based on the reproducibility of the individual mass signals when generating the reference spectra. An individual weight factor is derived for each mass signal of each reference spectrum during a similarity analysis of a sample spectrum. The weight factor is determined by the agreement with the mass signal of the sample spectrum, the agreement between the intensities and/or from the variation between the reference signals. For example, the smaller the variation of the intensity of the mass signal, the higher the individual weight factor. Mass signals that do not reproduce well receive a low individual weight factor. The individual weight factors of the mass signals of the reference spectra are added to determine a similarity indicator for each reference spectrum for the agreement with the sample spectrum. The reference spectra of a library are sorted according to the magnitude of the similarity indicators. The sorted reference spectra provides a list of designations of the microorganisms assigned to the reference spectra, sorted according to the similarity indicators.

Reference spectra having weights derived from statistical data of the repeat spectra are commonly referred to as "reference spectra with intrinsic weight" or "intrinsically weighted reference spectra". In contrast, reference spectra having weights derived from comparisons with other reference spectra of the spectral library or even from assessments by a microbiology specialist or technician are commonly referred to as "reference spectra with extrinsic weight".

DE 100 38 694 A1 to W. Kallow et al. discloses a method for generating extrinsically weighted reference spectra. The weights of the individual mass signals are derived from the frequency with which mass signals occur in the other reference spectra of the library. This method increases the ability to distinguish between reference spectra for the similarity analyses. For example, a mass signal that occurs in a single reference spectrum receives a maximum weight because the mass signal can accurately identify the microbe. Where a mass signal occurs indiscriminately with the same intensity in each of the reference spectra, however, the mass signal receives a weight zero. This type of reference spectra is disadvantageous for the validation of spectrum libraries, particularly when further reference spectra are to be added to an already validated library. The whole library must then be weighted anew and validated, where the validation is performed for all of the reference spectra. In addition, identifying the subspecies can be difficult where the measuring signal that distinguishes between the subspecies of a species has a low weight due to a coincidental presence of the same mass signal in many other, hardly related reference spectra. As the complexity of a reference library increases, this type of weight of individual signals becomes less and less usable.

U.S. Published Application 2004/0234952 discloses a method for expanding the library with a distinguishing spectrum for each pair of similar reference spectra. The distinguishing spectrum distinguishes between corresponding microbes in order to increase the distinguishability of reference spectra of subspecies. The distinguishing spectra have weights for the individual mass signals which emphasize a difference between the intensity of the mass signal and the intensity of the second reference spectrum. The differentiation therefore increases the ability to differentiate between reference spectra, while mass signals which have approximately the same intensity in both reference spectra have low weights. The permanent addition of such distinguishing spectra to the library, however, typically requires the library to be re-validated. These distinguishing spectra are also extrinsically weighed reference spectra.

Simple mass spectrometric identification methods can have a high success rate, even where weights for the mass signal of the reference spectra are not used. Typically, it is advantageous to generate the spectra under standardized conditions to cultivate the colony, to prepare the sample on the sample support, and to acquire the mass spectrum in order to determine both the reference spectra and the sample spectra, while preventing variations in the technical or biological method parameters. This measure alone already leads to an improved identification. Mass value and intensity value variations and weights, for example, do not need to be stored in the reference spectra. This can decrease the size of the library and increase the speed of the similarity analysis. A method for the adjustment of the frequently slightly shifted mass scales of the repeat spectra with respect to each other has been described above. Since many mass signals occur in only some of the repeat measurements, but can nevertheless contribute to the identification, the percentage of occurrences of a mass signal above a detection threshold should be noted. This number (hereinafter "occurrence ratio") gives the percentage of the repeat spectra in which the mass signal occurs. A mass signal therefore has three entries: averaged mass, averaged intensity, and occurrence ratio.

During the similarity analysis, each reference spectrum is examined to determine how many of the mass signals agree in each case with those of the microbe spectrum within a specified mass tolerance. A first partial measure for the similarity is determined by dividing the number of matches by the number of mass signals in the reference spectrum. A second measure is determined by dividing the number of matches by the number of mass signals in the microbe spectrum. A third partial measure can be derived from the intensity similarity between the mass signals that agree. The product of the three partial measures provides the similarity indicator. A refinement can be introduced by counting each match with the occurrence ratio of the mass signal, i.e. with a number which is possibly less than one. An extremely fast running algorithm can be developed to perform this simple similarity analysis, for example, for thousands of reference spectra in a few seconds using a typical computer server. This algorithm can (as was proposed above in the case of weighted spectra) be adjusted to a maximum similarity indicator between, for example, the measured and the reference spectra, to a maximum similarity indicator of 3.00 for identical spectra. It is even possible to transform the similarity indicators in such a way that a similarity value of 2.00 can be considered to be an adequate minimum requirement for an identification. Typically, such a minimum requirement and a corresponding maximum value have a high psychological value for the acceptance of the method.

Today, medically and legally admissible (i.e., "validated" or "certified") libraries with reliable microbial reference mass spectra are formed in many locations, including many institutes of microbiology and also central governmental institutions for disease monitoring and prevention. For this work as well it is much simpler to acquire the spectra only under standardized conditions without variation of all method parameters.

Closely related microbes can be distinguished using the aforesaid methods where the microbial subspecies with proteins uniquely vary in terms of species and subspecies. One microbe spectrum, however, can have good matches with several reference spectra, exhibiting almost identical similarity indicators, although the reference spectra may look different, even to the human eye. The contributions of different mass signals can compensate one another in the computation of the similarity indicator, such that the subspecies, or even the species, cannot be identified. Reference spectra with similar indicators usually belong to closely related microbes at the genus, species or subspecies level.

A microbe can typically be identified by its genus or species. The microbe should be identified by its species or subspecies, however, when, for example, the species or the subspecies exhibit a substantially different pathogenicity, or need to be medically treated in a different way. In such a case, the species, subspecies of even biovarieties like serotypes need to be accurately identified.

What is needed therefore is a method for identifying microbes by their mass spectra, with which the microbes can be identified down to the level of species or subspecies even where their reference spectra exhibit almost the same indicators.

SUMMARY OF THE INVENTION

According to a first aspect of the invention, a dual-stage method is provided for identifying at least one microbe. The microbe can be identified by its species or its subspecies even, for example, where different species and/or subspecies within a library have substantially similar reference mass spectra. During a first stage of the method, a first similarity analysis is performed by calculating similarity indicators indicative of similarities between the reference mass spectra and the microbial mass spectrum. During a second stage of the method, a temporary library is compiled of new reference mass spectra in a selected group. The new reference mass spectra are substantially similar to the microbial mass spectrum. Mass entries of the new reference mass spectra are each provided with a distinguishing weight used to determine how closely each new reference mass spectra matches, and thus identifies, the mass spectra of the sample microbe. The distinguishing weights are determined by comparing the new reference mass spectra with each other, and then emphasizing differences between the new reference mass spectra. A second similarity analysis is performed using the new reference mass spectra and the distinguishing weights. Upon completion of the identification, the temporary library may be erased such that the library of reference mass spectra remains unchanged. When a library is changed, as set forth above, it typically must be re-validated/re-certified. Advantageously, therefore, a library used according to this method can retain its, for example, IVD-CE certification. In some embodiment, a test can be performed between the first and the second stages to determine whether the first stage identified the microbe with adequate specificity.

According to a second aspect of the invention, a dual-stage method is provided for identifying a microbe by, for example, its species or its subspecies. The method includes measuring a mass spectrum of the microbe using a mass spectrometer, calculating indicators for similarities between reference mass spectra in a library and the measured mass spectrum, selecting a group of reference mass spectra similar to the measured mass spectrum, determining a distinguishing weight for each mass signal of the reference mass spectra in the group, where the distinguishing weights emphasize differences between the reference mass spectra in the group, and calculating indicators for similarities between the reference mass spectra in the group and the measured mass spectrum as a function of the distinguishing weights.

The first stage of the method includes measuring the mass spectrum of the microbe and calculating the similarity indicators. In some circumstances, the first stage may adequately identify the microbe being sampled. When different microbes have similar mass spectra, however, an adequate identification may not be possible. In such circumstances, the first stage can compile a "hit" list of microbe names that correspond to reference spectra that are substantially similar to the spectra of the microbe being sampled. The hit list of microbes can be arranged in order of decreasing similarity indicators.

The second stage of the method includes selecting the group of reference mass spectra, determining the distinguishing weight for each mass signal, and calculating similarity indicators. The selected group of reference mass spectra includes the reference spectra that are most similar (i.e., substantially identical) to the sample spectrum. For example, six or ten of the reference spectra may be selected with the highest similarity indicators. Alternatively, the reference spectra with the highest similarity indicators within a specified maximum difference (predetermined range) can be selected. In another example, each reference spectra in a subspecies or a strain of this microbe can be selected where the similar reference spectra predominantly correspond to a single microbe species. Different quantities of selected reference spectra can be included in the group depending on the application and the variation of the similarity indicators. For example, the group can include three to twenty, preferably four to ten, selected reference spectra. In some cases, the group can even include more than twenty reference spectra. Where the library includes a large quantity of reference spectra and each has the same subspecies or the same species, which would all come under the selection rule for the group and would cause the group to become too large, the selection can be limited to reference spectra labeled as being "typical". Such labeling is included in the library.

A processor can be programmed to determine the distinguishing weights, for example, by analyzing and emphasizing the differences in the reference spectra. Where a mass signal is included in one reference spectrum in the group, for example, a relatively high distinguishing weight is selected. The mass signal here can also have a low intensity. Where the mass signal is included in two of the reference spectra in the group, for example, a moderately high distinguishing weight is selected. Where intensities of the mass signals in the two reference spectra are significantly different, for example, higher distinguishing weights can be selected. Where the intensities are substantially equal, however, lower distinguishing weights are selected. Where a mass signal is included in each reference spectra in the group with a substantially identical intensity, for example, a distinguishing weight of zero can be selected, because such a mass signal likely cannot contribute to the identification. Moderately high distinguishing weights can be distributed for significantly different intensities of a mass signal which occurs in each of the reference spectra. A developer with some experience in the development of identification methods will be able to program a processor to perform the first and the second stages of the method. The distinguishing weights, as set forth above, are not permanently stored in the library of the reference spectra.

The distinguishing weights generally permit the second stage of the dual-stage method to adequately identify a microbe, for example, by a specified minimum difference between the highest similarity indicator and the second highest. A user (e.g., a technician), however, can make a final decision as to whether the identification is adequate. The technician can also restart the second stage with a different selected group of reference spectra.

In some embodiments, a test can be performed between the first and the second stages to determine whether the first stage adequately identified the sampled microbe. The test can be performed automatically by analyzing, for example, the differences between the highest similarity indicators while taking into account an absolute value of each indicator. The test can alternatively be performed manually. The technician, for example, may review microbe designations, similarity indicators and other information included in the hit list of the most similar reference spectra. In some circumstances, personal knowledge and/or other supplemental information may also be used during the review of the hit list. To review the hit list, the technician assesses, for example, whether a more finely graduated identification is needed due to different pathogenicity of the subspecies. Where it is determined that the identification made by the first stage is inadequate, the technician can start the second stage of the method. The technician can alternatively bypass the computer processing and manually preselect the group of the reference spectra. The technician can also manually select a reference spectrum which is classified as being typical for a species or a subspecies.

The selection of the groups of the most similar reference spectra and the determination of the distinguishing weights can be performed in fractions of a second. The distinguishing weights therefore can be temporarily stored. The temporary storage of the distinguishing weights has several advantages. For example, the library of reference spectra is not burdened with the storage of the distinguishing weights. The unaltered library does not need to be re-certified. In addition, changed groups of reference spectra with finer and finer differences can be selected for a sample spectrum such that the identification method is automatically adapted for libraries that continuously expand with new reference spectra.

These and other objects, features and advantages of the present invention will become more apparent in light of the following detailed description of preferred embodiments thereof, as illustrated in the accompanying drawings.

BRIEF DESCRIPTION OF THE DRAWING

The FIGURE illustrates a process flow of a method according to an aspect of the invention.

DETAILED DESCRIPTION OF THE INVENTION

One or more microbe sample may be identified using a dual-stage identification method that analyzes similarities between microbe spectra and reference spectra of a reference library.

During a first stage of the method, an identification can be performed using, for example, one of the methods described in the "Background" section herein. For example, a mass spectrum of the microbe is measured using a mass spectrometer. Indicators of similarities between the reference mass spectra in a library of reference mass spectra and the measured mass spectrum are calculated. The similarity indicators can be calculated using any suitable algorithm. The reference spectra in the library can be weighted either intrinsically or extrinsically.

In some embodiments, a test can be performed to determine whether the first stage has adequately identified the sample microbe. When the sample microbe has been adequately identified, a second stage of the method does not need to be performed.

During the second stage of the method, a group of reference spectra are selected which are substantially similar to the sample spectrum. The group of reference spectra can include, for example, the reference spectra with substantially identical indicators identified at the end of the first stage (e.g., the reference spectra included in the hit list). Alternatively, the group can include the reference spectra with the fixed numbers of the most similar reference spectra, or the reference spectra from one or more of the subspecies and strains identified at the end of the first stage. Distinguishing weights for mass signals of the reference spectra are derived to emphasize differences between the reference spectra in the group. The distinguishing weights are not, however, stored in the reference library. Rather, a small library of new reference spectra is formed, for example, that accurately corresponds to the masses and the intensities of the reference spectra in the group, and includes the distinguishing weights. A second stage similarity analysis is performed using the small library of new reference spectra with their newly derived distinguishing weights for the mass signals, i.e. with these extrinsically weighted reference spectra. The distinguishing weights are used to provide a more accurate sample microbe identification of the subspecies or the strain.

The algorithms for the similarity calculations in the first stage can be adapted for the similarity calculations in the second stage. For example, the first stage algorithms can be used by swapping the intrinsic or the extrinsic weights provided by the library for the distinguishing weights for the group of the new reference spectra.

The selected group of reference spectra can be stored in a computer memory. Once the distinguishing weights have been determined, they can be entered into the reference spectra in the group. The reference spectra in the library remains, therefore, unchanged. The temporarily stored group of reference spectra with distinguishing weights can then be made available for the similarity analysis as a new, small special library.

The distinguishing weights for the individual mass signals of the reference spectra in the selected group are determined by automatically analyzing differences in the reference spectra using, for example, a computer program. The distinguishing weights are derived to emphasize the differences between the mass signals. A higher distinguishing weight is assigned where a mass signal or its intensity infrequently reoccurs in the reference spectra. A lower distinguishing weight value is assigned where a mass signal or its intensity frequently reoccurs in the reference spectra. For example, a mass signal is assigned a relatively high value (e.g., 1,000 as compared to a normal value of 100) where the mass signal is present in a single reference spectrum. Here, the distinguishing weight affectively characterizes the subspecies. In another example, a mass signal is assigned a value of zero where the mass signal is present in each of the reference spectra in a group having the same intensity. In still another example, a mass signal is assigned a moderate distinguishing weight value such as 300 where two mass signals have the same intensities, or 400 to 600 where the two mass signals have slightly different intensities. Moderately low distinguishing weights can be distributed where the mass signal is present in each of the reference spectra and has intensities which are more or less, but in any case different.

The library of reference spectra may include in some embodiments occurrence ratio values, rather than weights for the individual mass signals. In this case, the distinguishing weights can be entered into the field(s) for the occurrence ratio values in the relevant similarity indicator algorithms. Such a swap of terms is possible because the occurrence ratios are typically used in a manner similar to that of the distinguishing weights. The same algorithms for the calculation of the similarity indicators therefore can also be used in the second stage.

According to one aspect of the invention, a method is provided for identifying a microbe based on a library of reference spectra. The library of reference spectra may be formed by (i) acquiring and cultivating known strains of microbes, (ii) sampling tiny quantities of the microbes, (iii) preparing a number of (e.g., ten) samples of each microbe on a mass spectrometric sample support, and (iv) acquiring a number of mass spectra (e.g., five) from each of the samples. In this example, the acquisition of the fifty mass spectra for each microbe strain takes approximately five minutes to complete. The large number of repeat spectra is determined because the processes of sample preparation with crystallization of a matrix substance and ion formation by MALDI may be difficult to accurately repeat, and good reference spectra are obtained by averaging many mass spectra together. A high number of repeat spectra also provides more reliable values for the occurrence ratios; i.e. the percentages of the presence of the mass signals above threshold.

Masses of the individual mass signals can shift slightly from spectrum to spectrum as a result of a desorption and ionization process for the generation of the ions in a MALDI time-of-flight mass spectrometer operated in linear mode. To accommodate this shift, the mass scales of the repeat spectra may be adjusted with respect to each other using the previously described method disclosed in DE 10 2004 051 043 A1 to M. Kostrzewa et al. Smaller mass tolerance intervals therefore can be used for the determination of the matches described below; e.g., 250 instead of 1,000 millionths of the mass (ppm).

The adjusted repeat spectra are used to automatically determine average mass values, average intensities and occurrence ratios for each mass signal (i.e., for mass signals that occur once, several times or in each of the repeat spectra). The occurrence ratios are indicative of how often a mass signal occurs above a measuring threshold in the repeat spectra. An occurrence ratio has a value of 1.00 (i.e., 100%), for example, where the mass signal is present in each of the repeat spectra. The reference spectrum combined from each of the repeat spectra is limited to a maximum of seventy mass signals by removing (i) each of the mass signals below a fixed threshold for the occurrence ratio (e.g., 15%), and (ii) the mass signals with the lowest intensities. In some cases, there may be less than 70 mass entries in a reference spectrum where, after removal of the noise signals which are characterized by low occurrence ratios, fewer than 70 mass signals remain.

In one embodiment, a reference spectrum of the library includes the mass averages, the intensity averages and the occurrence ratios for each of the seventy mass signals, in addition to the designations of the microbe species, subspecies, and strain. Alternatively, the reference spectrum may also include numerical values for calculating the similarity indicators, and/or the number of all mass signals weighted with the occurrence ratios. The reference spectra may still further include notes on the origin of the strains and the laboratory which acquired the spectra, which is typically necessary for validations. References to a special pathogenicity of the microbes, ecological harmfulness in waters, toxicity in food, harmfulness in bioprocesses, etc. may also be included. The references are preferably maintained in an encrypted form that can be used for an automated test. The test is used to determine whether the second stage should be performed to provide a more detailed identification. Treating methods for pathogens or environmental pests may also be included with corresponding codings. Where the reference spectra of several strains of the same subspecies (or species, where, e.g., no subspecies are known) are available in the library, one or even two of the reference spectra can be marked as particularly typical. These "typical" reference spectra can then be selected for the group of reference spectra in the second stage. Two reference spectra can be labeled as "typical", for example, where the strains of the subspecies exhibit two significantly different groups of reference spectra, the reference spectra in each group being similar to one another.

Additional libraries with particularly relevant reference spectra thereto can be compiled for various fields such as clinical infection diagnostics, monitoring of rivers and lakes, hygiene investigations, etc. The term "library" hereinafter shall include such special libraries.

In order to identify the sample microbe, the microbe is initially cultivated into a colony. The colony can be cultivated using, for example, the afore-described standardized method used to cultivate the reference spectra. The sample is transferred to a sample support of a mass spectrometer. This portion of the sample is also prepared using a matrix solution. A mass spectrum of the prepared sample is measured using the mass spectrometer. Several mass spectra are preferably measured such that they can be averaged to provide a "sample spectrum". The sample spectrum can be limited to, for example, a maximum of approximately 100 mass signals.

During the first stage of the identification method, a first similarity analysis is performed by calculating indicators for the similarities of the reference spectra in the library to the sample spectrum. The calculation is based from three partial measures. A first partial measure of the similarity indicator is represented by the number of mass signals which agree ("match") within a mass tolerance interval in the microbe spectrum and reference spectrum, divided by the number of mass signals in the reference spectrum. Each of the mass signals, however, is counted pro rata with its occurrence ratio. The mass tolerance interval (e.g., 250 ppm) is provided in absolute terms in atomic mass units (or dalton), or as a relative value in ppm (parts per million). A second partial measure is provided from the number of matches divided by the number of mass signals in the microbe spectrum, which again may be counted pro rata with the occurrence ratios. A third partial measure is calculated from the similarity of the respective intensities of the mass signals which agree in relation to one another, where the occurrence ratios are again taken into account by multiplication. The third partial measure is normalized for each of the mass signals such that when the intensities are equal, the partial measure has a value of, for example, approximately 1.00.

The three partial measures are multiplied together to provide an indicator of the similarity between the reference and the microbe spectrums. The similarity indicator may have a maximum value of approximately 1.00 because each of the three partial measures may have a maximum value of approximately 1.00.

Experiments have shown that reliable microbe identification generally has a similarity value greater than approximately 0.10. In some embodiments, however, a transformation may be undertaken by multiplying by 1,000 and subsequently taking a logarithmic value which provides a maximum similarity indicator of approximately 3.00 for identical spectra, and a minimum similarity indicator of approximately 2.00 for an identification. The present invention, however, is not limited to the aforesaid embodiment. In particular, any suitable transformations may be applied where it is shown to be practicable.

The aforesaid calculations for the similarity indicators can be performed using a relatively fast working algorithm such that, for example, a typical computer can compute thousands of similarity indicators in a few seconds. Typical single-stage methods output a list of the best similarities, with the names of the corresponding microbe species, subspecies and strains, arranged, for example, in order of decreasing similarity indicators. This list can be dispensed with at this place for dual-stage methods.

During the second stage of the method, a group of reference spectra is selected. The selection can include a fixed number of reference spectra of maximum similarity, where the fixed number lies, for example, between three and twenty, and preferably between four and ten. Alternatively, the selection can be based on the differences between the similarity indicators, the number being determined by marked jumps in the graduation of the similarity indicators, or by the sum of the differences between the decreasing similarity indicators. The selection can also include the reference spectra of each of the subspecies and strains of a microbe species (or each of the species of a genus), where such a microbe species (or genus) is suggested by the most similar reference spectra of the first stage. When applicable, the most typical reference spectra for species or subspecies can be selected where they are marked as such in the reference library.

The distinguishing weights for the selected group of reference spectra are determined as set forth above. The distinguishing weights are entered in a column for the occurrence ratios. Since these values enter into the count in both the dividends (numerator) as well as the divisors (denominator) of the partial indicators, the afore-described method for the calculation of the similarity indicators may be used.

The second stage is performed with the group of new reference spectra by calculating indicators for the similarity of each new reference spectra using the sample spectrum. The group of the new reference spectra is included in a special library made available to an algorithm for the similarity analysis. A hit list of the most similar reference spectra is output, where the list is arranged, for example, in order of descending similarity indicators. The distinguishing weights in the new reference spectra typically provide an unambiguous identification to be made after the second stage. As set forth above, the identification is given by a specified minimum difference between the highest similarity indicator and, for example, the second highest similarity indicator. The final decision on whether an identification is adequate, however, may be determined by the technician. The technician can also restart the second stage with a new group of reference spectra.

The second stage does not need to be preformed where a sample microbe has already been adequately identified using the first stage. An identification test therefore may be performed between the first and the second stages to determine whether the second stage should be started. Depending on the objective of the analysis, an adequate identification can be provided where a majority of similar reference spectra identify the microbe species. In addition, a precise identification of the subspecies or the strain may not be necessary where, for example, the species and the subspecies have similar degrees of lethality and/or similar methods of treatment. In such an example, the second stage may be omitted. The test can be performed manually by the technician or automatically.

The technician can perform the test using the hit list of reference spectra compiled by the first stage. Where the largest similarity indicators are substantially similar, the technician can decide whether the second stage needs to be performed. Knowledge on the different degrees of harmfulness of the microbe subspecies can particularly contribute to this decision. For example, where the technician decides to continue the method, he can also manually select the group of reference spectra that are used for the calculation of new distinguishing weights. The selection can be carried out, for example, by clicking on the reference spectra in the list on a computer screen. The technician can also manually select each of the species or subspecies related to a strain. In most cases, the first stage provides many subspecies of a single microbe species as the most similar reference spectra. The technician, however, can supplement this group by including reference spectra of additional subspecies. After the selection, the technician can start the second stage of the method.

The test that determines whether the microbe has to been adequately identified can also be performed automatically, for example, by analyzing the differences between the largest similarity indicators or by their absolute value. Where the differences are below a specified tolerance limit, or where the values are below the minimum value for the similarity indicator, a group of reference spectra is automatically selected, and the second stage of the method is started. This detailed analysis may not be necessary, however, where individual subspecies of an otherwise harmless microbe species creates no particular hazard.

The dual-stage method may be autonomous and automatically performed where, for example, (i) the identification test to determine whether the identification made by the first stage is adequate is performed automatically, or (ii) no identification test is performed between the first and the second stages. Advantageously, with such an autonomous method, the technician need not make intermediate assessments during the identification. In addition, this method consumes little additional processing time; e.g., fractions of a second to at most a few seconds longer than the previous single-stage methods. An automatic and dynamic adaptation of the method to the individual sample spectrum is provided because this influences the selection of the reference spectra for the second stage via the similarity indicators of the first stage. The identification is automatically made more detailed as the reference library grows. The technician therefore merely needs to assess the identification after the second stage. An identification of the species, the subspecies or even the strain provided by this method can be reliable enough such that the technician can accept the identification without performing additional steps and checks.

An additional advantage of the dual-stage method is that the distinguishing weights do not need to be permanently stored in the reference library. Rather, the distinguishing weights are calculated during each identification. The re-calculation of the distinguishing weights permits the method to be dynamically adapted so the library is supplemented with additional reference spectra.

Microbe identification methods are typically tested in large-scale studies in which accurately known microbe samples are analyzed in different laboratories. These studies determine the error rates of the methods. Studies of this type have already produced very good results for known single-stage identification methods, where even in disputed cases the identifications have frequently had to be corrected. The experiences from these studies have been considered during the development of the dual-stage method.

In the dual-stage method, the mass spectra of the microbes may be determined, for example, in mass spectrometers with ionization by matrix-assisted laser desorption (MALDI). Alternatively, it is also possible to ionize digestion liquids of microbes by electrospraying, either at atmospheric pressure or at lower pressures of a few thousand pascals. This type of ionization generates strong superimpositions of multiply charged ions, which typically use a mass spectrometer with a relatively high resolution. The multiply charged ions are included in a mass range between, for example, approximately 600 daltons and 1600 daltons. Doubly, triply and quadruply charged ions with the mass-to-charge ratios of $m/z=1,501, 1,001$ and $751$ daltons are predominantly formed from a protein with a mass of, for example, 3,000 daltons. Ions having, for example, roughly 10 to 20-fold charges, with a maximum of, for example, 14-fold charges, are formed from a protein with a mass of, for example, 15,000 daltons. The 50 to 100 proteins therefore can form a heap of ions in a relatively narrow mass range. The proteins, however, can usually be easily resolved in a mass spectrometer with relatively high mass resolving power of $R>40,000$. The charge z can be determined from the distances between the mass signals of an isotope group, and a list of the protein ions can be compiled in which the ions of different charge levels and different isotopic compositions are combined in one entry. This list forms the spectrum of the microbes. The mass spectrometer can also be a time-of-flight mass spectrometer with orthogonal injection of the ions (OTOF-MS), ion cyclotron resonance mass spectrometers (ICR-MS), or any other high resolution mass spectrometer.

The digestion liquids of the microbes can also be introduced to the electrospray ion source by a short HPLC column; i.e. separated by liquid chromatography. Even a low chromatographic separation may substantially reduce the jumble of mass signals such that the computed combination of the different charge levels and isotopic signals of the protein ions will succeed better.

In some embodiments, it may also be possible to conduct a physical charge reduction, rather than computing the combination of the charge levels of the ions. The charge reduction may be performed by bringing together positively charged protein ions and suitable negatively charged ions in an ion reactor located between an electrospray ion source and an analyzer. This can result in a deprotonation of the protein ions. Since the reaction cross-sections for the deprotonation are proportional to the square $z^2$ of the charge number z, the process may be ended when, for example, practically only singly charged ions remain. These have to be introduced into the mass spectrometer, however, which must be able to cope with a large range of masses m/z.

Additional methods for ionization may be used. For example, one advantageous method is atmospheric pressure chemical ionization (APCI). The molecules are introduced to the chemical ionization by atomizing a liquid and vaporizing the droplets, or by weak, non-ionizing laser desorption ("laser ablation"). The chemical ionization supplies, for example, practically only singly charged ions and is thus very favorable. However, this also requires a mass spectrometer with an adequately large mass range.

Although the present invention has been illustrated and described with respect to several preferred embodiments thereof, various changes, omissions and additions to the form and detail thereof, may be made therein, without departing from the spirit and scope of the invention.

What is claimed is:

1. A method for automatically identifying a microbe, comprising:
   measuring a mass spectrum of the microbe using a mass spectrometer;
   calculating indicators for similarities between reference mass spectra in a library and the measured mass spectrum;
   selecting a group of reference mass spectra similar to the measured mass spectrum;
   determining a distinguishing weight for each mass signal of the reference mass spectra in the group, where the distinguishing weights emphasize differences between the reference mass spectra in the group; and
   calculating indicators for similarities between the reference mass spectra in the group and the measured mass spectrum as a function of the distinguishing weights.

2. The method of claim 1, where
   the step of determining the distinguishing weight is a function of a frequency of the mass signal for each of the reference mass spectra in the group, and of differences in intensities of the mass signal; and
   a mass signal of a reference spectrum receives a lower distinguishing weight when
      a similar mass signal is included in the reference mass spectra in the group; or
      differences between intensity of the mass signal and intensities of similar mass signals in other reference mass spectra of the group are relatively small.

3. The method of claim 1, where the group of reference mass spectra is selected to include between about three and twenty reference mass spectra with the highest similarity indicators.

4. The method of claim 1, where the group of reference mass spectra is selected to include between about four and ten reference mass spectra with the highest similarity indicators.

5. The method of claim 1, where the group of reference mass spectra is selected to include reference mass spectra with similarity indicators that are different from a highest similarity indicator by a predetermined number.

6. The method of claim 1, where the group of reference mass spectra is selected to include reference mass spectra identified as most similar using the calculated similarity indicators.

7. The method of claim 6, where the group of reference mass spectra is selected to include reference mass spectra labeled as typical when the most similar reference mass spectra are from at least one of a single strain and a single species.

8. The method of claim 1, further comprising performing a test to determine whether the microbe is adequately identified from the calculated similarity indicators between the reference mass spectra and the measured mass spectrum.

9. The method of claim 8, where the test is performed automatically by analyzing the similarity indicators between the reference mass spectra and the measured mass spectrum.

10. The method of claim 8, where the test is performed as a function of relative harmfulness of or types of treatment for an identified species or an identified subspecies.

11. The method of claim 1, where an entry for each of the reference mass spectra in the library includes a mass, an intensity and an occurrence ratio.

12. The method of claim 1, where the similarity indicators between the reference mass spectra and the measured mass spectrum are calculated from a number of mass signals that agree within specified mass tolerance values, and from similarities of the intensities of the mass signals that agree.

13. The method of claim 1, where the similarity indicators between the reference mass spectra and the measured mass include a product of two quotients of a number of matches divided by total number of mass signals in the reference mass spectra and the measured mass spectra respectively.

14. The method of claim 13, where the numbers of matches and the total number of mass signals are each weighted by its occurrence ratio.

15. The method of claim 1, where the mass spectrometer comprises a mass spectrometer with ionization by matrix-assisted laser desorption.

16. The method of claim 1, where the mass spectrometer comprises a mass spectrometer with ionization by electro-spraying.

17. The method of claim 1, where the mass spectrometer comprises a mass spectrometer with ionization by chemical ionization at atmospheric pressure.

* * * * *